United States Patent
Beinhocker

(10) Patent No.: US 9,373,234 B1
(45) Date of Patent: Jun. 21, 2016

(54) SECURITY TAPE FOR INTRUSION/EXTRUSION BOUNDARY DETECTION

(71) Applicant: 3D FUSE SARL, Geneva (CH)

(72) Inventor: Gilbert D. Beinhocker, Belmont, MA (US)

(73) Assignee: 3D FUSE TECHNOLOGY INC., Belmont, MA (US)

( * ) Notice: Subject to any disclaimer, the term of this patent is extended or adjusted under 35 U.S.C. 154(b) by 17 days.

(21) Appl. No.: 14/551,578

(22) Filed: Jan. 20, 2015

(51) Int. Cl.
*G08B 13/12* (2006.01)
*A61F 2/00* (2006.01)

(52) U.S. Cl.
CPC ........... *G08B 13/126* (2013.01); *A61B 2562/02* (2013.01); *A61B 2562/0209* (2013.01); *A61F 2002/0068* (2013.01)

(58) Field of Classification Search
CPC ............. G08B 13/126; A61B 2562/02; A61B 2002/0068
See application file for complete search history.

(56) References Cited

U.S. PATENT DOCUMENTS

| | | | |
|---|---|---|---|
| 2,311,613 | A | 2/1943 | Slayter |
| 3,320,114 | A | 5/1967 | Schulz |
| 3,634,845 | A | 1/1972 | Colman |
| 3,696,373 | A | 10/1972 | Dunn et al. |

(Continued)

FOREIGN PATENT DOCUMENTS

| | | |
|---|---|---|
| DE | 485 035 | 10/1929 |
| EP | 0 401 153 | 5/1990 |

(Continued)

OTHER PUBLICATIONS

Bonner, Robert C., "Remarks of U.S. Customs Commissioner Robert C. Bonner*: U.S. Customs and Border Protection C-TPAT Conferenence San Francisco, California Oct. 30, 2003," http://www.cpb.gov/xp/cgov/newsroom/commissioner/ speeches_statements/Oct30,2003.xml (8 pages).

(Continued)

*Primary Examiner* — Van Trieu
(74) *Attorney, Agent, or Firm* — Preti Flaherty Beliveau & Pachios LLP

(57) ABSTRACT

A security tape comprises a mesh sensor strip in which a filament is woven or otherwise provided to serve as a single continuous signal path across substantially the entire area of the mesh strip. The filament may be an electrical wire or an optical fiber to carry, respectively, an electrical signal or an optical signal. A layer of flexible insulative material is bonded to each side of the mesh strip by an adhesive on the bonding surface of each of the layers. During bonding of the layers to the mesh strip, the adhesive flows into the mesh structure and structurally fixes the filament in its position in the mesh. The mesh sensor strip and bonded layers can be cut to any desired length and each end of the filament is connectable to respective connector units. One connector unit is connected to a signal source, and the other connector unit is connected to a signal receiver. A break in the filament will cause a loss of constant continuous conduction and therefore loss of signal received by the receiver thereby indicating an alarm condition. The security tape protects against both intrusion and extrusion events across any boundary of a volumetric space which cause breakage of the signal path and trigger an alarm indication. The absence of a required real-time electrical or optical conduction signal signifies an alarm state, hence the system is fail-safe.

17 Claims, 12 Drawing Sheets

(56) References Cited

U.S. PATENT DOCUMENTS

| | | | |
|---|---|---|---|
| 3,714,644 A | 1/1973 | Hellstrom | |
| 3,947,837 A | 3/1976 | Bitterice | |
| 4,095,872 A | 6/1978 | Stieff et al. | |
| 4,100,536 A | 7/1978 | Ball et al. | |
| 4,118,211 A | 10/1978 | Au Coin et al. | |
| 4,161,348 A | 7/1979 | Ulrich | |
| 4,175,827 A | 11/1979 | McMahon | |
| 4,195,907 A | 4/1980 | Zamja et al. | |
| 4,217,488 A | 8/1980 | Hubbard | |
| 4,228,425 A | 10/1980 | Cooke | |
| 4,234,875 A | 11/1980 | Williams | |
| 4,297,684 A | 10/1981 | Butter | |
| 4,318,088 A | 3/1982 | Hunter | |
| 4,367,460 A | 1/1983 | Hodara | |
| 4,447,123 A | 5/1984 | Page et al. | |
| 4,488,269 A | 12/1984 | Robinson et al. | |
| 4,526,752 A | 7/1985 | Perlman et al. | |
| 4,538,527 A | 9/1985 | Kitchen | |
| 4,573,202 A | 2/1986 | Lee | |
| 4,603,252 A | 7/1986 | Malek et al. | |
| 4,772,092 A | 9/1988 | Hofer et al. | |
| 4,801,213 A | 1/1989 | Frey et al. | |
| 4,867,820 A | 9/1989 | Jacobson et al. | |
| 4,908,510 A | 3/1990 | Huggins et al. | |
| 4,931,771 A | 6/1990 | Kahn | |
| 4,935,723 A | 6/1990 | Vallance | |
| 4,972,176 A | 11/1990 | Vallance | |
| 5,003,374 A | 3/1991 | Vokoun, III | |
| 5,049,855 A | 9/1991 | Slemon et al. | |
| 5,081,363 A | 1/1992 | Tetzlaff et al. | |
| 5,119,862 A | 6/1992 | Maimets et al. | |
| 5,177,805 A | 1/1993 | Groger et al. | |
| 5,180,060 A | 1/1993 | Forti et al. | |
| 5,194,847 A | 3/1993 | Taylor et al. | |
| 5,309,533 A | 5/1994 | Bonniau et al. | |
| 5,323,011 A | 6/1994 | Suter et al. | |
| 5,355,208 A | 10/1994 | Crawford et al. | |
| 5,359,416 A | 10/1994 | Mueller | |
| 5,461,364 A | 10/1995 | Sanford, Jr. et al. | |
| 5,568,124 A | 10/1996 | Joyce et al. | |
| 5,592,149 A | 1/1997 | Alizi | |
| 5,594,418 A * | 1/1997 | Martin | G08B 13/126 200/61.93 |
| 5,609,952 A | 3/1997 | Weiss | |
| 5,648,724 A | 7/1997 | Yankielun et al. | |
| 5,656,996 A | 8/1997 | Houser | |
| 5,769,232 A | 6/1998 | Cash et al. | |
| 5,790,025 A | 8/1998 | Amer et al. | |
| 5,808,554 A | 9/1998 | Shuminov | |
| 5,918,268 A | 6/1999 | Lukas et al. | |
| 6,002,501 A | 12/1999 | Smith et al. | |
| 6,065,870 A | 5/2000 | Nunez | |
| 6,155,120 A * | 12/2000 | Taylor | A61B 5/1036 73/862.046 |
| 6,213,167 B1 | 4/2001 | Greenland | |
| 6,331,678 B1 * | 12/2001 | Wang | H05K 1/0271 174/253 |
| 6,487,895 B2 | 12/2002 | Brooker et al. | |
| 6,556,138 B1 | 4/2003 | Sliva et al. | |
| 6,879,257 B2 | 4/2005 | Hisano et al. | |
| 6,891,470 B2 | 5/2005 | Bohinc, Jr. | |
| 6,919,803 B2 | 7/2005 | Breed | |
| 7,015,823 B1 | 3/2006 | Gillen et al. | |
| 7,098,784 B2 | 8/2006 | Easley et al. | |
| 7,137,525 B2 | 11/2006 | Gibney | |
| 7,211,783 B2 | 5/2007 | Beinhocker | |
| 7,352,284 B2 | 4/2008 | Krill | |
| 7,394,060 B2 | 7/2008 | Beinhocker | |
| 7,482,924 B1 | 1/2009 | Beinhocker | |
| 7,595,452 B2 | 9/2009 | Kirstein et al. | |
| 7,702,358 B2 | 4/2010 | Meyers | |
| 7,706,641 B2 | 4/2010 | Murphy et al. | |
| 7,732,517 B2 | 6/2010 | Fukushima | |
| 7,905,999 B2 * | 3/2011 | Petyt | C12Q 1/001 204/403.01 |
| 7,922,883 B2 * | 4/2011 | Petyt | C12Q 1/001 204/403.01 |
| 8,437,748 B2 | 5/2013 | Brisebois et al. | |
| 8,501,103 B2 | 8/2013 | Bangera et al. | |
| 8,715,576 B2 | 5/2014 | Bangera et al. | |
| 2002/0089434 A1 | 7/2002 | Ghazarian | |
| 2003/0151509 A1 | 8/2003 | Iannotti et al. | |
| 2003/0174059 A1 | 9/2003 | Reeves | |
| 2003/0193032 A1 | 10/2003 | Marshall | |
| 2004/0037091 A1 | 2/2004 | Guy | |
| 2004/0046660 A1 | 3/2004 | Ando | |
| 2004/0047142 A1 | 3/2004 | Goslee | |
| 2004/0056767 A1 | 3/2004 | Porter | |
| 2006/0151656 A1 | 7/2006 | Gallagher et al. | |
| 2006/0244616 A1 | 11/2006 | Hill | |
| 2007/0001844 A1 | 1/2007 | Krill | |
| 2008/0075934 A1 | 3/2008 | Barlow, Jr. et al. | |
| 2008/0211669 A1 | 9/2008 | Dagher et al. | |
| 2009/0115607 A1 | 5/2009 | Beinhocker | |
| 2010/0097215 A1 | 4/2010 | Locher | |
| 2010/0170616 A1 | 7/2010 | Boss et al. | |
| 2010/0289651 A1 | 11/2010 | Beinhocker | |
| 2012/0133507 A1 | 5/2012 | Bangera et al. | |
| 2013/0300431 A1 | 11/2013 | Beinhocker | |

FOREIGN PATENT DOCUMENTS

| | | |
|---|---|---|
| EP | 2 180 453 | 10/2008 |
| FR | 2619237 | 2/1989 |
| GB | 13359 | 1/1914 |
| WO | WO 93/11513 | 6/1993 |
| WO | WO 93/23648 | 11/1993 |
| WO | WO 98/26388 | 6/1998 |

OTHER PUBLICATIONS

Kimura et al., "New Techniques to Apply Optical Fiber Image Guide to Nuclear Facilities," J. Nuc. Sci. and Tech., vol. 39, No. 6, pp. 603-607 (Jun. 2002).

Lu et al., "Gamma-induced attenuation in normal single-mode and multimode, Ge-doped and P-doped optical fibers: A fiber optic dosimeter for low dose levels," Published on the NRC Research Press Web site on May 11, 2000, Can. J. Phys. vol. 78, pp. 89-97.

Nucsafe Inc., Introduction "Fiber Sensing Technology—The Long and Short of It," http://nucsafe.com/Puma/introduction.htm May 21, 2004, p. 1 of 1.

Nucsafe Inc., "Why Neutrons," http://nucsafe.com/Puma/why_neutrons.htm, May 21, 2004, p. 1 of 1.

Nucsafe Inc., "Guardian CRMS," http://nucsafe.com/Puma/guardian_crms.htm, pgs. May 21, 2004, 6 pages.

Nucsafe Inc., "Fiber Optic Facility," http://nucsafe.com/Puma/fiber_facilities.htm, May 21, 2004, 2 pages.

Nucsafe Inc., "Detecting Neutrons," http://nucsafe.com/Puma/detecting_neutrons.htm, May 21, 2004, 3 pages.

Nucsafe Inc., "Photonics," http://nucsafe.com/Puma/pr_photonicsspectra.htm, Jul. 9, 2004, 2 pages.

Nucsafe Inc., "Tech Transfer," http://nucsafe.com/Puma/pr_techtransfer.htm, Jul. 9, 2004, 2 pages.

Nucsafe Inc., "Press Release—Frist Applauds Job Creation at Oak Ridge Based-Nucsafe," http://nucsafe.com/Puma/pr_knoxnews.htm, Jul. 9, 2004, 3 pages.

Nucsafe Inc., "Optical Properties," http://nucsafe.com/Puma/properties_of_scintillating_fibe.htm, Jan. 12, 2005, p. 1 of 1.

Ott, Melanie N., "Radiation Effects Data on Commercially Available Optical Fiber: Database Summary," Nuclear Science and Radiation Effects Conference, Phoenix, Arizona, NSREC 2002, Data Workshop Proceedings, July, 8 pages (we believe this to be accurate).

Ott, Melanie N., "Radiation Effects Expected for Fiber Laser/Amplifier Rare Earth Doped Optical Fiber," NASA Survey Report (Mar. 26, 2004), 7 pages.

Simpson, Doug, "US port security system set for launch," www.boston.com/news/nation/articles/2004/03/25/us_port_security_system_set_for_launch?mode=PF, pp. 2 of 2.

Giallorenzi et al. Optical fiber sensor technology, IEEE Journal of Quantum Electronics, vol. QE-18, No. 4 (Apr. 1982), pp. 626-665.

* cited by examiner

SECURITY TAPE FOR INTRUSION/EXTRUSION BOUNDARY DETECTION

STATEMENT REGARDING FEDERALLY SPONSORED RESEARCH OR DEVELOPMENT

N/A

CROSS REFERENCE TO RELATED APPLICATIONS

This application is related to a number of issued patents and pending patent applications, in the name of the inventor of the present application, that relate to tamper proof containers and other enclosures and security systems for containers, enclosures, pipelines and other structures. The issued U.S. patents are: U.S. Pat. Nos. 7,211,783; 6,995,353; 7,394,060; 7,608,812; 7,332,728; 7,098,444; 7,482,924; 7,619,226; 7,856,157; 7,924,166, 8,207,861 and 8,653,971.

BACKGROUND OF THE INVENTION

As is known, in order to detect an intrusion into, or out of, a protected volumetric space, a sensor sheet is provided to enclose the volume of interest which has a continuous electrical or optical signal path disposed in the sheet and substantially encompassing the full extent thereof. An electrical signal, in the case of a wire path, or an optical signal, in the case of an optical fiber path, is introduced to one end of the signal path, and the signal is received at the opposite end of the signal path. The presence of a signal indicates a normal or non-alarm state. In the event of a break or other interruption in the signal path, the loss or diminution of the signal is detected and signifies an alarm condition. In the case of an optical fiber signal path, the optical fiber can be sensitive to incident nuclear radiation that causes a reduction in the amplitude and/or characteristics of the optical signal and which can be detected as an indication of an alarm condition.

Current fabrication techniques for installation of sensor sheets involve first applying a resin layer to the surface of the object to be enclosed, e.g., the interior walls of a cargo container or the outer surface of a pipeline. The resin must be allowed to dry to a certain point and then, within a specified time window, i.e., before the resin hardens, the sensor sheet is to be laid on top. A top layer of resin is thereafter applied and allowed to dry to hold fast the sensor sheet in a protective sandwich construction.

A sensor security detector tape is described in U.S. Pat. No. 8,653,971 which includes a material strip with predetermined width and length and first and second ends. At least one signal path is provided in the material strip where each signal path has a first end and a second end. First and second connectors are coupled to the first and second ends, respectively, of the signal paths. The signal path may be either an electrical wire or an optical fiber.

In another embodiment, a sensor security detector tape includes a material strip having a predetermined width and a predetermined length and first and second ends and a plurality of signal paths where each signal path has a first end and a second end. First and second connectors are coupled to the first and second ends, respectively, of the signal paths.

In another embodiment, a plurality of conductive paths are connected at one end to a multiplexing circuit to which an input signal is applied for propagation along all of the conductive paths. The other end of the plurality of conductive paths is connected to a logical circuit which provides an output signal. A break in any one of the plurality of conductive paths will cause a loss of conduction in the broken paths and a change in the output signal from the logical circuit. The logical circuit in one implementation is an AND gate. The gate output is in one state when all of the conductive paths are intact and carrying a signal. The output of the gate will change state in the absence of conduction in any one or more of the paths. This change of state is indicative of an alarm condition. The logical circuit can be of other forms known to those of skill in the art to provide the intended function. The multiplexer and the AND gate or other logical circuit can be housed within respective connectors to which the plurality of signal paths are coupled.

BRIEF SUMMARY OF THE INVENTION

A security tape in accordance with the invention includes a mesh sensor strip which can be similar to that described in the aforesaid U.S. Pat. No. 8,653,971. The mesh sensor strip is woven of polyester or other fibers that provide a flexible mesh in which a filament is woven or otherwise provided to serve as a single continuous signal path across substantially the entire area of the mesh strip. The filament may be an electrical wire or an optical fiber to carry, respectively, an electrical signal or an optical signal. A layer of flexible insulative material is bonded to each side of the mesh strip by an adhesive on the bonding surface of each of the layers. During bonding of the layers to the mesh strip, the adhesive flows into the mesh structure and fixes the filament in its position in the mesh.

The layers are joined to the mesh strip by a laminating process by which the adhesive bonds to the mesh and some of the adhesive is squeezed into the interstices and/or fibers of the mesh. The adhesive in the mesh encases the filament in the mesh structure such that the filament remains in place in the mesh during flexing of the tape which can occur during the unrolling of the tape from a roll and during wrapping of an item to be protected. Additionally, the adhesive encased filament is protected from breakage during use. An item being wrapped can be subject to bending forces, such as torsional forces exerted on the opposing corners of a pallet, box or container being lifted. The tape constructed according to the invention can withstand such forces.

The layers bonded to the mesh strip extend beyond the side edges of the strip and are seemed or bonded together to enclose the mesh and isolate the mesh from moisture and other contaminants.

Each of the tape layers in one embodiment is composed of a rugged pressure sensitive plastic electrically insulative material such as PVC. An example of such tape material is 3M model EAD 825.

The mesh sensor strip and bonded layers can be cut to any desired length and each end of the filament is connectable to respective connector units. One connector unit is connected to a signal source, and the other connector unit is connected to a signal receiver. If the filament is an electrical wire, an electrical signal is introduced into the signal path defined by the filament and is received by the electrical receiver connected to the opposite end of the filament. A break in the filament will cause a loss of electrical conduction and loss of signal received by the electrical receiver thereby indicating an alarm condition. If the filament is an optical fiber, one connector unit is connected to an optical signal source and the other connector unit is connected to an optical receiver. A break in the optical fiber causes a loss of optical signal and again provides an alarm indication. Alternatively with respect to an optical signal, a pre-determined attenuation of the light signal may be detected and serve to indicate an alarm state as well as a total loss of the optical conduction signal.

The embodiment of the filament by the adhesive infused into the surrounding mesh protects the electrical filament which typically is of a very small diameter from breakage or damage due to bending or twisting of the tape during installation and use on an object being protected. The filament is also maintained in separated intended position in the fabric mesh. An electrical filament is typically about 100 microns in diameter and an optical filament is typically about 150 microns in diameter.

The security tape in accordance with the invention protects against both intrusion and extrusion events across a defined boundary, such as the wall of a pipe or container. An intrusion event can be for example an attempt at tampering with the object wrapped with the tape which would cause breakage of the filament and resulting signaling of an alarm condition. An extrusion event can be for example a fire or over pressure caused by a lithium ion or other battery in a package wrapped with the security tape, or for example a corrosion induced leakage in a pipe or the emission of radiation from the inside of a container or pipe in a nuclear power plant.

In one aspect the security tape can be wrapped around battery enclosures or electronic gear containing batteries which may catch fire or explode. A fire or explosion within a protected enclosure will cause breakage of the filament to thereby signal an alarm condition. This is especially important in securing high value electronic goods being shipped as air freight. Special fire suppression pallets are already in use. The novel security tape greatly facilitates efficient use of a fire suppression pallet because of the total enclosure of a package by the tape.

In another aspect, an optical fiber can be employed to detect different types of radiation and can be tailored to detect, for example, nuclear radiation. The use of specially doped optical fibers such as with Gadolinium 57 or Boron 6 facilitates detection of free thermal neutrons and signature emission particles to detect the presence of fissile material. In a further aspect the adhesive layers of material can act as a thermal insulator or barrier to prevent excess thermal expansion or shrinkage of the tape which could be caused by operating temperature variation which could damage or break the filament.

The invention can be embodied in covers or enclosures of various forms. For example, the invention can be made in sheets which can be stitched or bonded together to produce a pallet cover for covering products or objects on a shipping pallet of any geometric shape, such as found on ships, trucks or aircraft. A pallet cover in accordance with the invention provides security against intrusion or extrusion events and an alarm indication in the event of any such event.

BRIEF DESCRIPTION OF THE SEVERAL VIEWS OF THE DRAWINGS

Various aspects of at least one embodiment of the present invention are discussed below with reference to the accompanying figures. It will be appreciated that for simplicity and clarity of illustration, elements shown in the drawings have not necessarily been drawn accurately or to scale. For example, the dimensions of some of the elements may be exaggerated relative to other elements for clarity or several physical components may be included in one functional block or element. Further, where considered appropriate, reference numerals may be repeated among the drawings to indicate corresponding or analogous elements. For purposes of clarity, not every component may be labeled in every drawing. The figures are provided for the purposes of illustration and explanation and are not intended as a definition of the limits of the invention. In the figures.

DETAILED DESCRIPTION OF THE INVENTION

Figure 1:
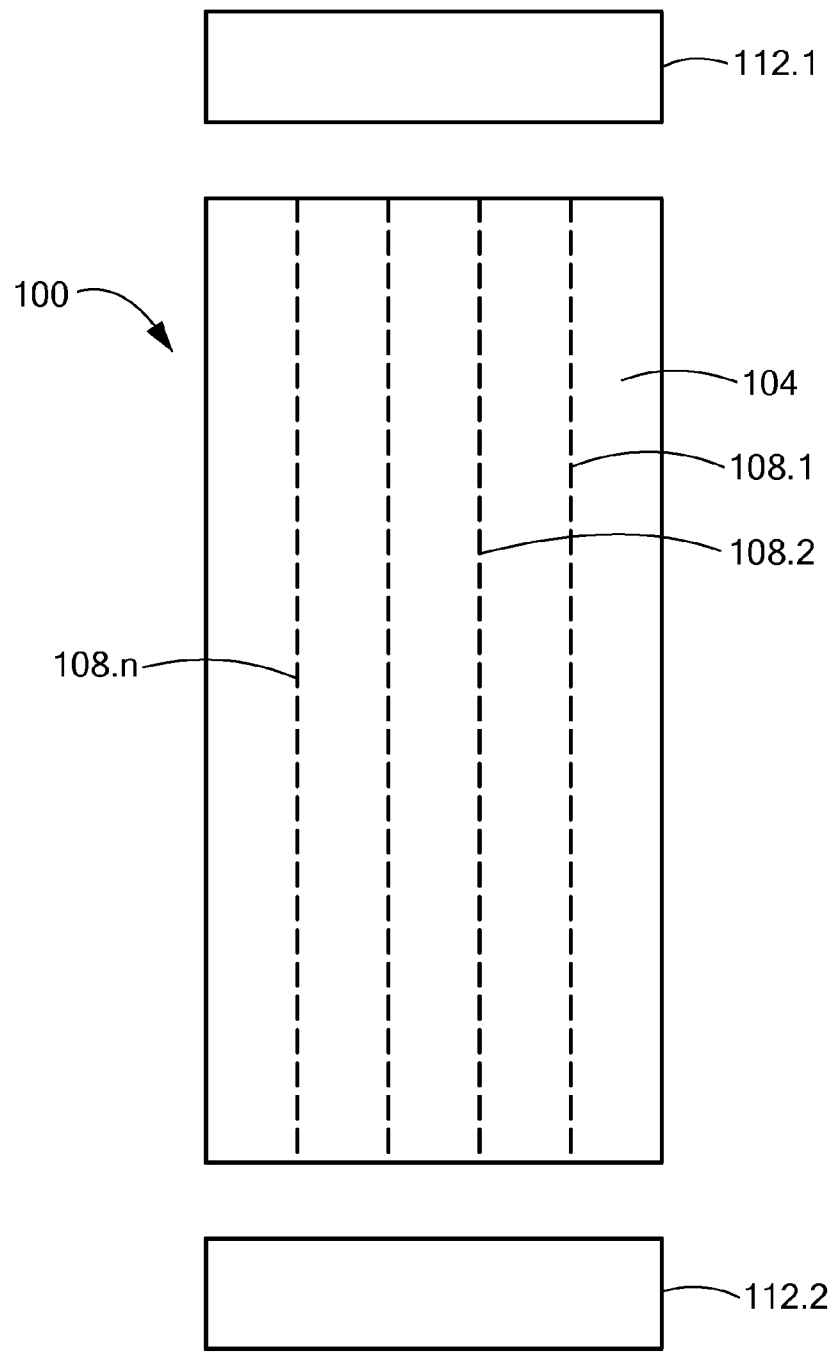
FIG. 1 is a schematic representation of a sensor tape structure in accordance with an embodiment of the present invention.

Further, each of U.S. Pat. Nos. 7,211,783; 6,995,353; 7,394,060; 7,608,812; 7,332,728; 7,098,444; 7,482,924; 7,619,226; 7,856,157, and 7,924,166, 8,207,861 and 8,653,971 is incorporated by reference herein in its entirety for all purposes.

In the following detailed description, numerous specific details are set forth in order to provide a thorough understanding of the embodiments of the present invention. It will be understood by those of ordinary skill in the art that these embodiments of the present invention may be practiced without some of these specific details. In other instances, well-known methods, procedures, components and structures may not have been described in detail so as not to obscure the embodiments of the present invention.

Prior to explaining at least one embodiment of the present invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein are for the purpose of description and should not be regarded as limiting.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Embodiments of the present invention relate to a an elongated flexible sensor security detector tape having a signal path provided therein by electrical wire or optical fiber and which extends between one end of the tape to the other end of the tape. In one embodiment, as will be described in more detail below, a plurality of electrical wires or optical fibers are disposed in the tape in a spaced relation, e.g., parallel to one another, across the width of the tape and extending along the length of the tape. The tape may include a non-conductive material in which the wires or optical fibers are woven or otherwise disposed in, for example, a polyester material. Protective layers of flexible material may be laminated on respective sides of the sensor tape to provide a laminated structure that is robust and that can be readily rolled and unrolled from a reel for efficiency of transport and for installation on a structure to be protected, e.g., by encapsulating any configuration of volumetric space, such as a pipeline, by spin-wrapping. Spin-wrapping is a well understood technique in the pipeline industry used to apply an insulation material to pipes in order to provide a solid coating, for example, a thermal-protecting coating. In addition to spin-wrapping the laminated sensor tape in sandwich fashion, an outer tough durable Kevlar or carbon based filament tape can be spin-wrapped in a second stage for added external protection. Additionally, a third outer sensor tape can be further applied to create a "detect and delay" sequence to allow responders additional time to reach the indicated intrusion/extrusion breach.

Additionally, after application by spin-wrapping, a protective resin coating can be applied over the sensor tape segments as an additional protective layer. Tuffset P resin, available from Isothane Ltd. in the United Kingdom, is one such resin available for this application.

In one embodiment of the present invention, a linear sensor tape segment 100 includes a material strip 104. A plurality of signal paths 108.$n$ are disposed either on, or within, the material strip 104, as shown in FIG. 1. The signal paths 108.$n$ may comprise electrical wires for carrying an electrical signal or optical fibers for carrying an optical signal. In one embodiment, the material strip 104 may be, but is not limited to, a non-conductive fabric material in which the wires or optical fibers may be woven or otherwise disposed. Here, the plurality of signal paths 108.$n$ are spaced across the width of the material strip 104, generally parallel to one another, but not electrically or optically coupled to one another. The electrical wires may or may not be individually insulated. The resolution distance between the signal paths 108.$n$ in the material strip 104 can be chosen as needed and, in one embodiment, is approximately 0.25 inches, although almost any distance as will fit the requirements can be chosen. The length of the linear sensor tape segment 100 may be cut to fit the particular application. Once cut to the desired length, two bridging connectors 112.1, 112.2 are coupled, respectively, to the ends of the material strip 104. The function of the bridging connectors 112.1, 112.2 will be described below.

Figure 2:
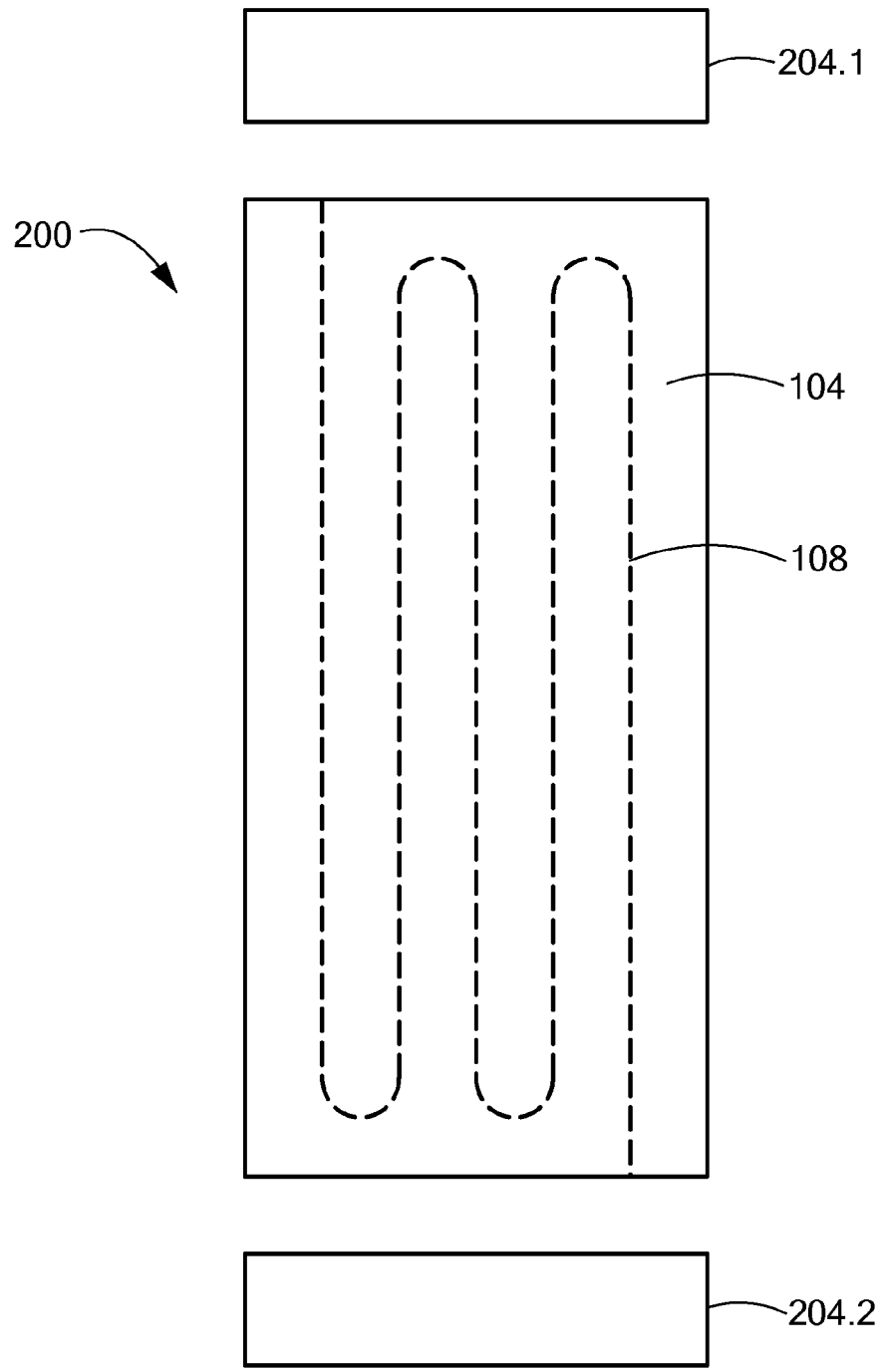
FIG. 2 is a schematic representation of a sensor tape structure in accordance with another embodiment of the present invention.

In another embodiment of the present invention, as shown in FIG. 2, a sinuous sensor tape segment 200 includes the material strip 104 with a sole signal path 108 comprising an electrical wire or an optical fiber. Here, the sole signal path 108 is distributed in a sinuous pattern across the width of the material strip 104. Two terminating connectors 204.1, 204.2 are coupled, respectively, to the ends of the material strip 104. The function of the terminating connectors 204.1, 204.2 will be described below.

Figure 12:
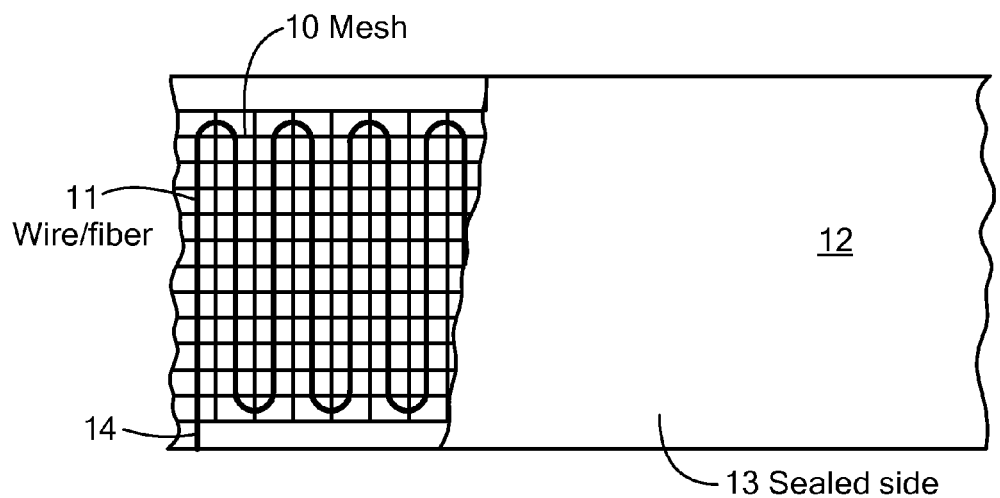
FIG. 12 is an embodiment of a sensor tape having a single filament.

One preferred embodiment is shown in FIG. 12 and comprises a flexible woven mesh 10 of polyester fibers and having a filament of 100 micron copper wire woven in the mesh. The filament is woven as a single continuous thread in an undulating pattern along the length of the mesh. The mesh fibers are 100-150 microns in diameter, as an example, and are woven with a thread count of 11 threads per inch, for example.

A first and a second layer 12 of electrically insulative material are adhesively bonded to respective sides of the mesh strip. The layers 12 are preferably wider than the width of mesh strip 10 to provide side portions 13 which are sealed together to enclose the mesh strip containing filament 11. Each of the layers 12 have a coating of adhesive on one surface thereof which is bonded to a respective side of the mesh strip. During bonding of layers 12 to mesh strip 10, the adhesive flows into the mesh structure to fix or lock the filament in its position in the mesh. In this manner, the filament cannot appreciably move during flexing of the sensor tape as can occur during unrolling of the tape from a roll or reel or during wrapping of the sensor tape on an item to be protected, or from handling or bending of the protected item.

The sensor tape composed of the mesh and bonded layers can be cut to any desired length and each end 14 of filament 11 is connectable to respective connector units. One connector unit is connected to a signal source, which may be an electrical receiver source if the filament is a wire, or an optical signal source if the filament is an optical fiber. The other connector unit is connected to a signal receiver, which if the filament is a wire is an electrical signal receiver or if the filament is an optical fiber is an optical signal receiver.

Figure 13:
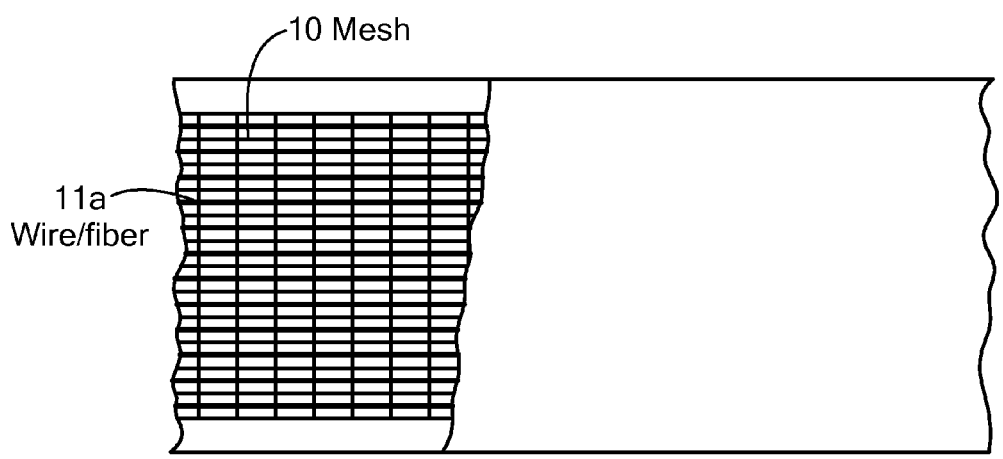
FIG. 13 is an embodiment of a sensor tape having multiple filaments.

Another preferred embodiment is shown in FIG. 13 which, as in FIG. 12, has a mesh covered by outer layers. The signal path is composed of a plurality of filaments 11$a$ woven in the mesh as a parallel separated array. The filaments 11$a$ are connected to connector units to form a single continuous signal path such as described with respect to FIG. 3A.

Figure 3A:
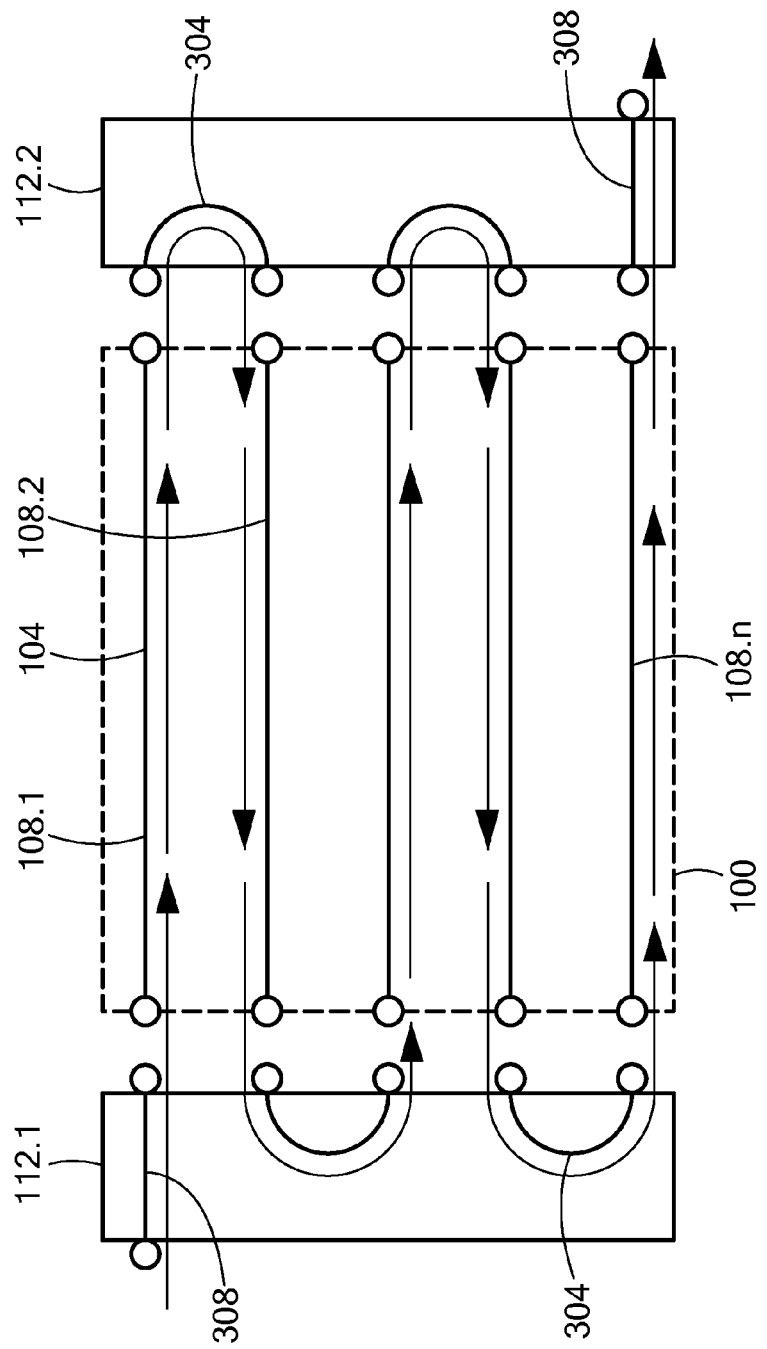
FIGS. 3A and 3B are electrical schematic representations of the sensor tape structures of FIGS. 1 and 2.

Referring now to FIG. 3A, each bridging connector 112.$n$ includes a plurality of jumper links 304 to electrically, or optically couple the signal paths 108.$n$ into a single continuous signal path, as represented by the arrows. The bridging connector 112 is provided at the end of each linear sensor tape segment 100 to bridge, i.e., interconnect, the signal paths 108.$n$, i.e., the wires or optical fibers in the linear sensor tape segment 100 to provide a single continuous signal path through the linear sensor tape segment 100 from one end to the other. The jumper links 304 are arranged to correspond with the signal paths 108.$n$ and the bridging connector 112 would be sized to match the width of the fabric 104. The bridging connector 112 also includes a pass-through link 308 that couples the single continuous signal path either to a signal source, a next sensor tape segment or a signal sensing system.

Figure 3B:
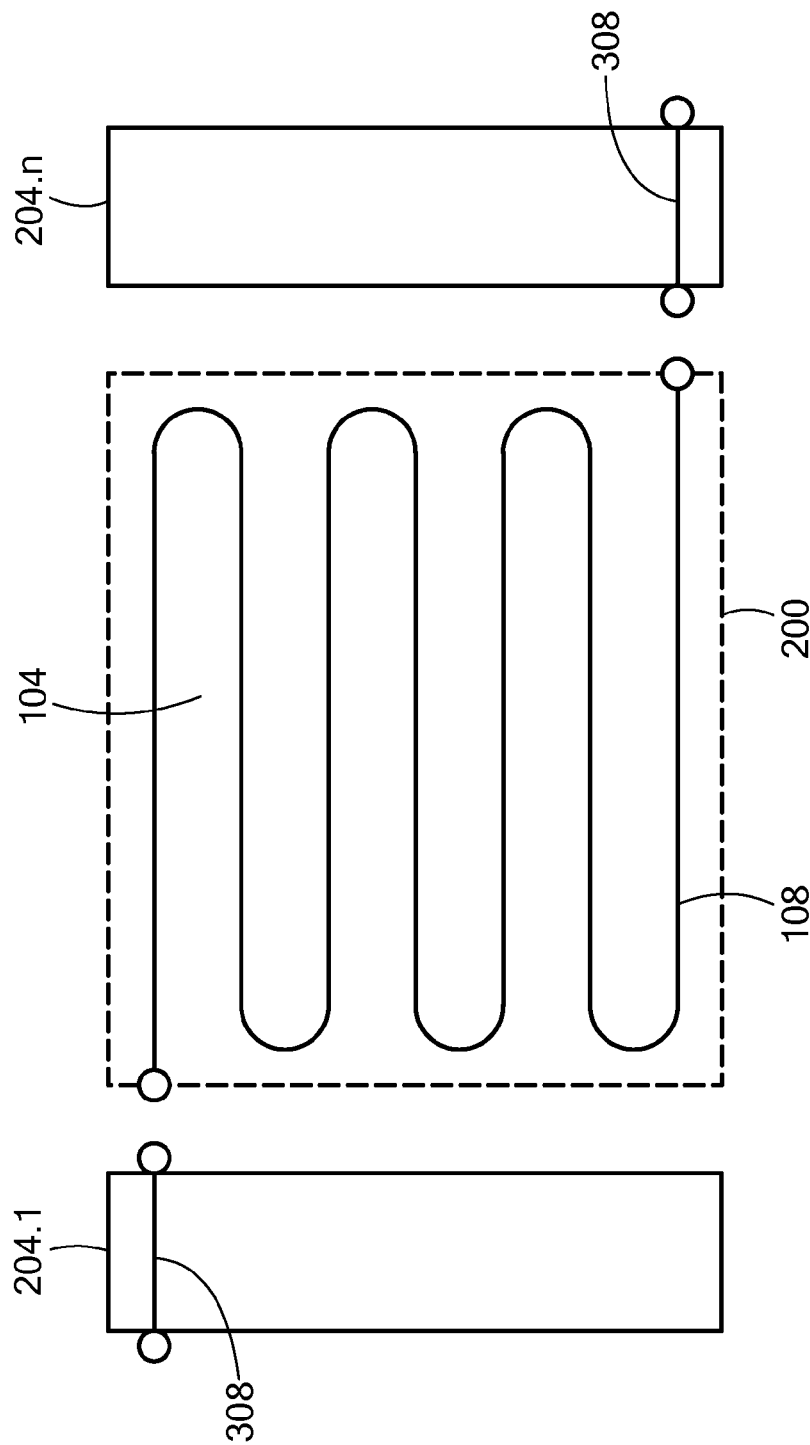

The terminating connector 204 includes a pass-through link 308, as shown in FIG. 3B, to provide an interface to the sole signal path 108. Of course, the terminating connector 204 is sized to match the material strip 104 and couple to the corresponding end of the sole signal path 108.

The connectors 112, 204 may be Flexible Printed Circuit (FPC) type connectors as available from many different vendors such as Tyco, Molex or Texas Instruments. As known to one of ordinary skill in the art, an FPC type connector will clamp onto the sensor tape segment and couple to the signal paths.

Figure 4:
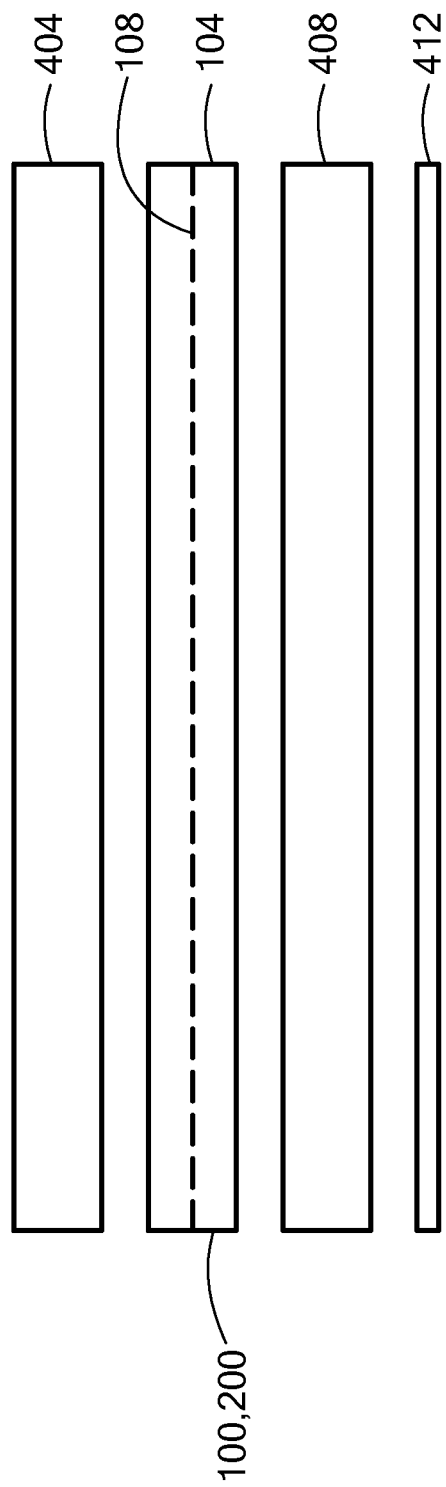
FIG. 4 is an exploded view of a sensor tape structure in accordance with an embodiment of the present invention.

A number of protective layers 404, 408 of a flexible material may be laminated on respective sides of either of the sensor tape segments 100, 200 to provide a laminated structure, as shown in FIG. 4 (in exploded view). Here, the signal path 108 is shown as being provided within the material strip 104 merely for ease of explanation although other embodiments as described herein are also applicable. The protective layer or layers 404, 408 are provided to protect the inner sensor tape segment 100, 200. The one or more protective layers 404, 408 of suitable material can be laminated or otherwise secured to each side of the sensor tape segment 100, 200 with the properties needed to suit a particular installation's requirements.

The protective layers 404, 408 may be, for example, silicone rubber or plastic and may be attached to respective sides of the sensor tape segment 100, 200 by any one of a number of mechanisms, including, but not limited to, gluing with an adhesive, heat bonding, pressure bonding, etc. The protective layers 404, 408 may be waterproof and resistant to other environmental and other contaminants to which they may be exposed. The protective layers may also have releasable layers of paper to be peeled off prior to application.

In one embodiment, an adhesive outer surface 412 may be provided to allow for initial bonding to the surface of, for example, a pipe, during installation of the tape, where the surface may or may not have a sheen layer of anti-corrosion film already applied.

One of skill in the art will understand that the number of protective layers 404, 408 may vary depending upon the needs of the application. Further, various combinations and sub-combinations of the protective layers 404, 408 in conjunction with the adhesive layer 412 are contemplated, for example, where the adhesive layer 412 is applied to the sensor tape 100, 200 without there being a protective layer 408 disposed between. In addition, a sensor tape 100, 200 may be "sandwiched" between two adhesive layers 412, with or without, protective layers on either side. Still further, a structure with multiple layers of sensor tape 100, 200 is also contemplated as being within the scope of this invention.

Figure 9:
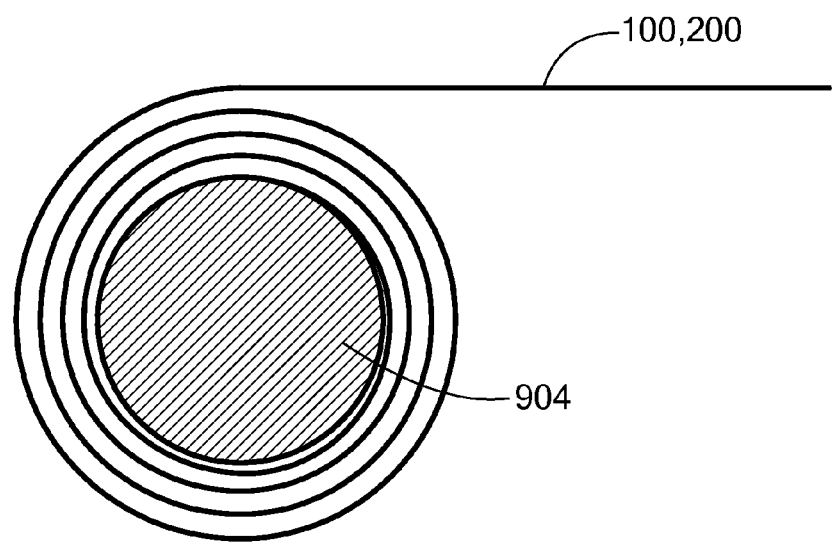
FIG. 9 is a representation of a spool of sensor tape in accordance with an embodiment of the present invention.

The sensor tape segment 100, 200 is fabricated in lengths suitable for spin wrapping or other processes of application onto an enclosure or protected space. In one embodiment, the tape segment 100, 200 is about 5-7 inches wide and about 250-300 feet long. The sensor tape 100, 200, with or without protective layers 404, 408, or an adhesive layer 412, may be provided on a spool 904, as shown in FIG. 9. Of course, one of ordinary skill will understand that any necessary release layers would be provided in order to allow for the unrolling of the sensor tape 100, 200 when being applied, as described below.

Figure 5A:
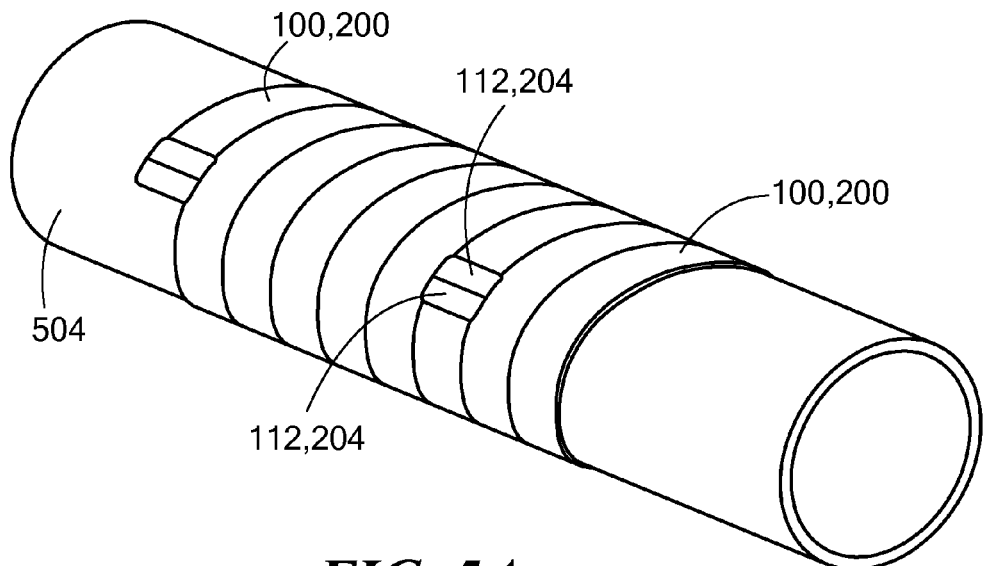
FIGS. 5A and 5B are representations of applications of an embodiment of the sensor tape structure in accordance with the present invention.
Figure 15:
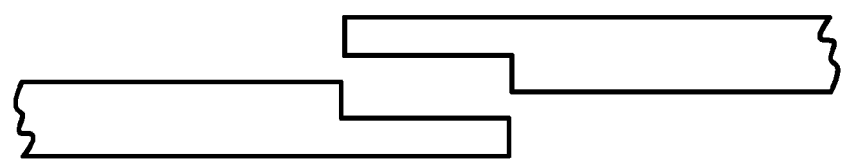
FIG. 15 is a cutaway schematic view of a tape having offset edges.

In one application, the sensor tape segments 100, 200 are wrapped around, for example, a pipeline or pipe section 504, as shown in FIG. 5A, to provide an effectively continuous wrapping. The sensor tape segments 100, 200 may be helically wrapped around the pipe section 504. The connectors 112, 204 of sequentially adjacent sensor tape segments 100, 200 are interconnected to provide a continuous signal path through the multiple tape segments. The wrapping can be guided on the irregular surface of a pipe by sensors to ensure edge-to-edge alignment of the tape to ensure a smooth continuous wrap. For example, a stripe or marker can be placed along the longitudinal edge of the tape and can be visually, by person, optical reader, or sensing machine, monitored to align the tape segments by optical recognition and feedback as would be understood by those of ordinary skill in the art. In addition, a raised edge such as shown in FIG. 15 may be provided on the tape segments and used to align segments when being applied.

Figure 5B:
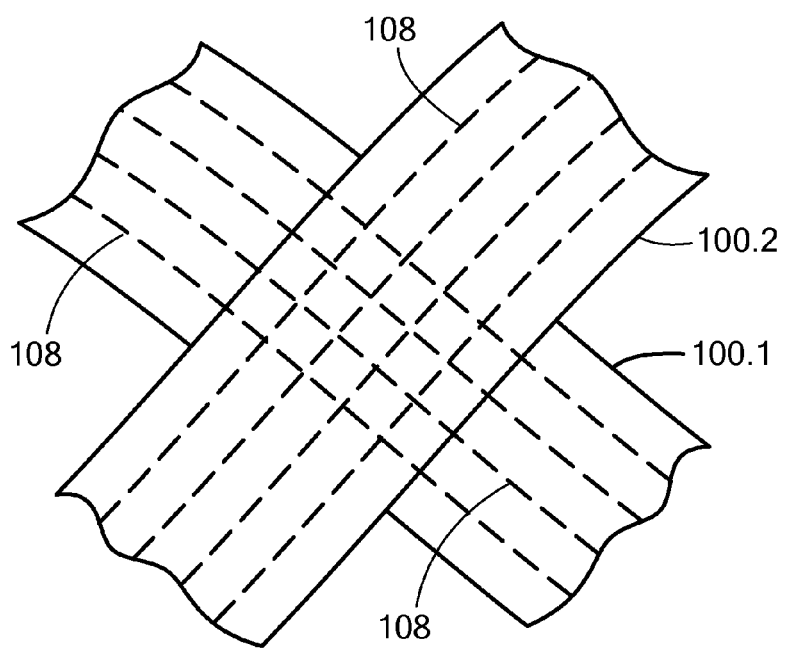

In another application, by applying a second sensor tape segment over a first tape segment in an offset manner, effective resolution can be improved to create a virtual solid wall of detection. Referring to FIG. 5B, for example, a first sensor tape segment 100.1 is placed, e.g., wrapped, in a first orientation about the item and a second sensor tape segment 100.2 is wrapped in a second orientation different from the first orientation, about a portion of the first sensor tape segment 100.1. As a result, a portion of the plurality of parallel signal paths 108 in the second sensor tape segment 100.2 cross a portion of the plurality of parallel signal paths 108 in the first sensor tape segment 100.1. Thus, a grid of signal paths is established which can effectively create a detection wall of very small resolution. Where the signal paths are ¼ inch apart, if applied at right angles to one another, an effective resolution of 1/16 square inch can be had as shown in FIG. 5B. Still further, the second tape segment 100.2 may be applied at any angle, not just a right angle, to the first tape segment 100.1.

Thus, if each of the multiple layers is geometrically offset from the others by a predetermined distance, the effective detection resolution is increased, i.e., the density of wires per square area is increased. Accordingly, any desired cost-effective detection resolution can be established. In principle, multiple offset layers can theoretically reduce the aperture of resolution to such a small opening that an effectively "solid wall" is provided that detects a breach, i.e., either an intrusion or extrusion, of any size.

Alternately, a single tape segment could be wrapped back on itself to effectuate the same grid of signal paths.

The sensor tape segment 100, 200 of the present invention can be readily installed in the field by spin wrapping onto pipe sections as they are being constructed into a pipeline. Alternatively, the sensor tape segment 100, 200 can be factory installed on sections of the pipe before it is transported to an installation site. This would likely be more economical for making smaller pipes such as those found in chemical plants or nuclear plants, for example.

An overcoating of polyurethane or other suitable material can be applied over the tape segments 100, 200 after being wrapped about the pipe 504 to protect against wear, abrasion and other adverse or damaging conditions to which the pipe 504 may be exposed.

The novel security tape may be embodied much like a usual roll of packing tape which can be wrapped around an object to be protected. The tape can be cut to a useful length and connected to signaling circuitry as discussed above.

Figure 11:
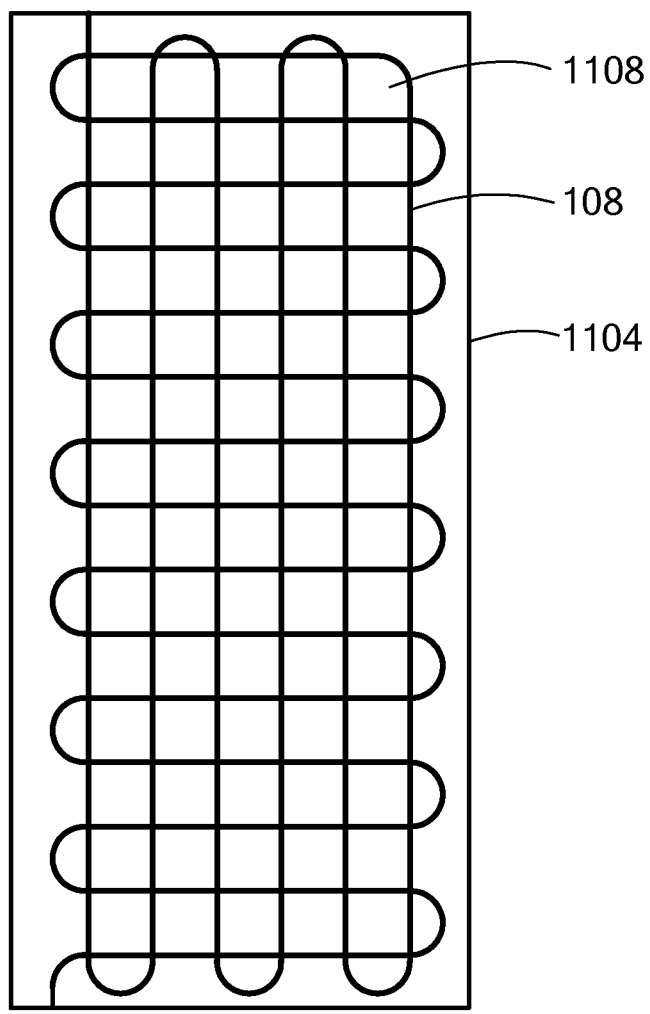
FIG. 11 is an alternate arrangement of a signal path in a sensor tape in accordance with embodiments of the present invention.

There are variations on the sole signal path where, as shown in FIG. 11, a hybrid approach is used that includes parallel rows with interleaved sinuous paths. Depending upon the spacing, a single path is provided with finer detection resolution as compared to only parallel paths or only a sinuous path.

Each embodiment of the present invention can be used to detect the presence or absence of an event such as, for example, a bullet hole in the pipeline 504 or thieves placing a "bleeder" tube into the pipeline 504 (intrusion events) or a corrosion induced leak or a corrosive hole forming in the pipeline 504 and leaking fluid (extrusion events) or a manufacturing defect in the pipe. Similarly, an intrusion into a secured cargo container or an extrusion event, such as, radiation detection from within an enclosed space, may be detected.

In operation, the absence of conduction of an electrical or optical signal provides a self-monitoring feature that does not require initiating an active signal to interrogate a secured system in order to obtain a response. A fail-safe passive "always on" conducting signal that fails to be detected in a continuous manner indicates a "problem," be it the detection of an intrusion event or an extrusion event or failure of the system components such as its power supply. This detection information may be provided and monitored in real-time to enable either the determination of a location of an event at a specific pipe segment or the presence of a failed component in the sensor tape segment which, in effect, shuts the system down. Thus, a failed component is treated as an intrusion or extrusion event. Location information can be provided for example by a unique signal address for each pipe segment.

Figure 6:
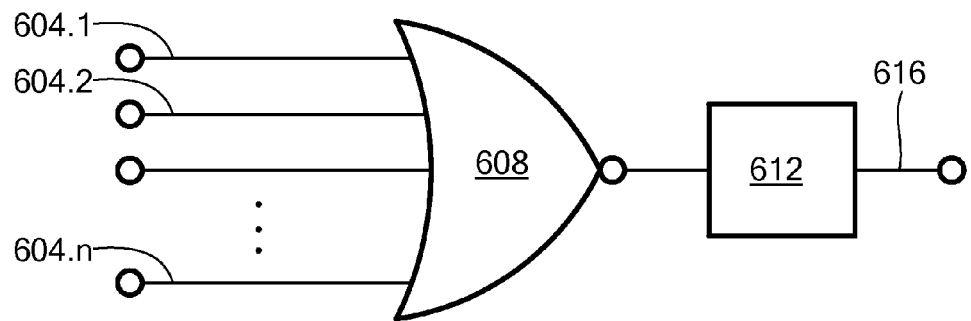
FIG. 6 is a block diagram of an intrusion/extrusion detection system in accordance with an embodiment of the present invention.

In one embodiment, an output 604.*n* of each respective tape segment or strip 100, 200 is fed to a NOR gate function 608 and then to a processor 612, such as shown in FIG. 6. In a normal non-alarm condition, a signal is received from each tape segment 100, 200 and is applied to the processor 612 to signify the normal state. If an incursion or excursion event occurs that causes a break in the signal path 108 of even a single wire of a tape segment 100, 200, the signal 604.*n* from that segment 100, 200 will cease, which will cause the NOR gate function 608 to present an alarm signal to the processor 612 which will produce an alarm output 616. One of ordinary skill in the art will understand that the NOR gate function 608 may be provided by discrete components or could be performed by integrated circuits within the processor 612 if all output signals 604.*n* are provided to the processor 612.

Figure 7:
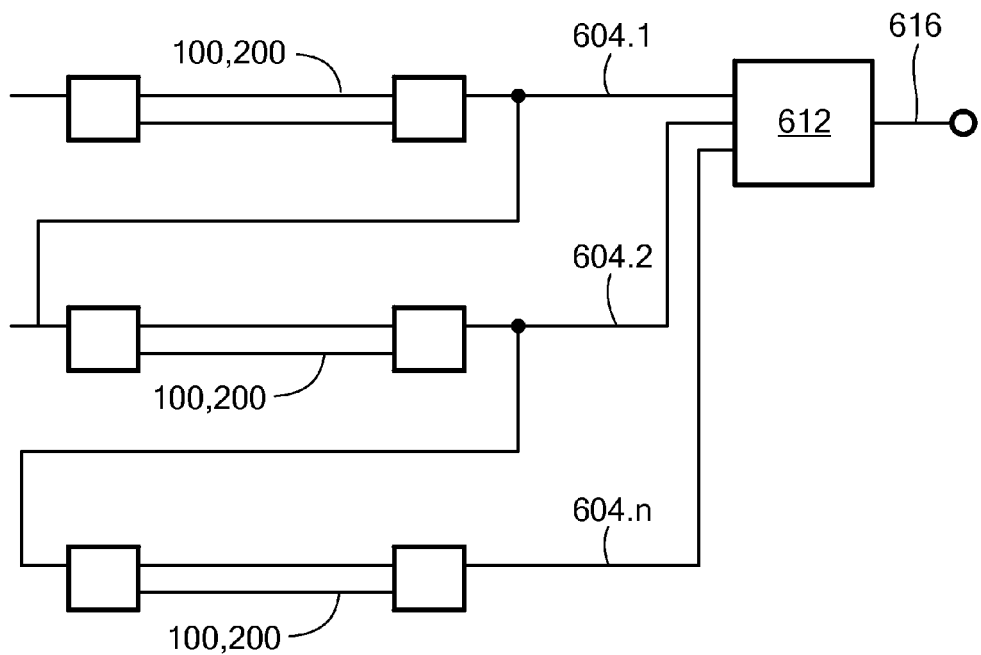
FIG. 7 is a block diagram of an intrusion/extrusion detection system in accordance with an embodiment of the present invention.

In another embodiment, the processor 612 can identify the tape segment where the alarm event has been detected and can provide other data as may be required or desirable. Referring now to FIG. 7, a number of sensor tapes 100, 200 are connected in series where the output signal 604.*n* of one is the input to the next. The output signal 604.*n* of each sensor tape is also submitted to the processor 612 to be processed as described above where the lack of an output signal indicates an event and the specific sensor tape 100, 200 that has detected the event can be determined.

Figure 8:
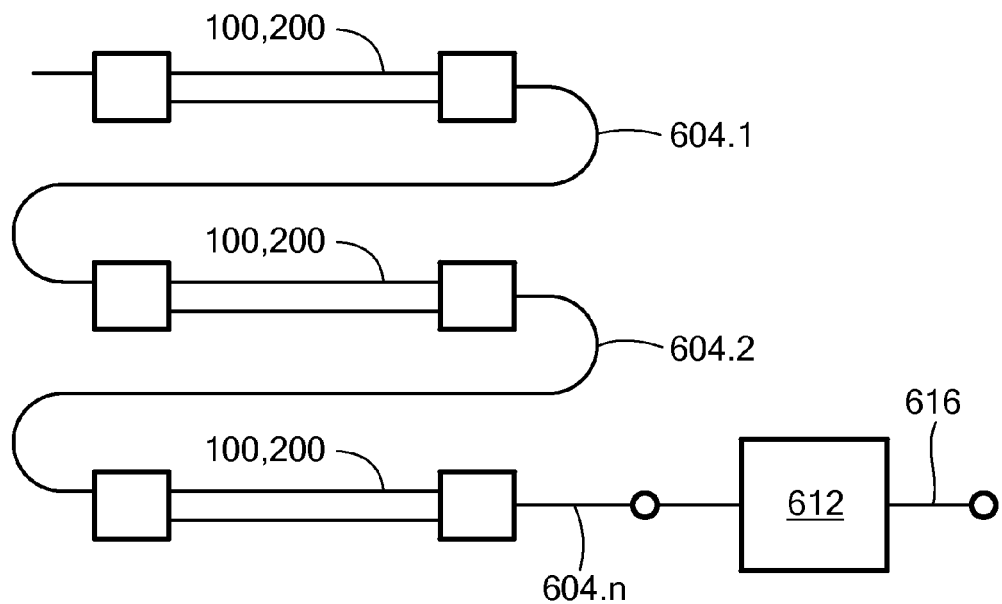
FIG. 8 is a block diagram of an intrusion/extrusion detection system in accordance with an embodiment of the present invention.

Alternately, where a number of sensor tapes 100, 200 are connected in series, as shown in FIG. 8, a single output 604.*n* may be provided to the processor 612. If the signal on the single output 604.*n* ceases, the processor 612 will raise the alarm output 616 as detecting an event although the location of the event, i.e., the specific sensor tape 100, 200 that detected the event, in this particular embodiment, cannot be determined.

Information regarding the alarm event can be transmitted to one or more local and/or remote receiving sites by any wired or wireless modality provided in conjunction with the processor 612.

Figure 10:
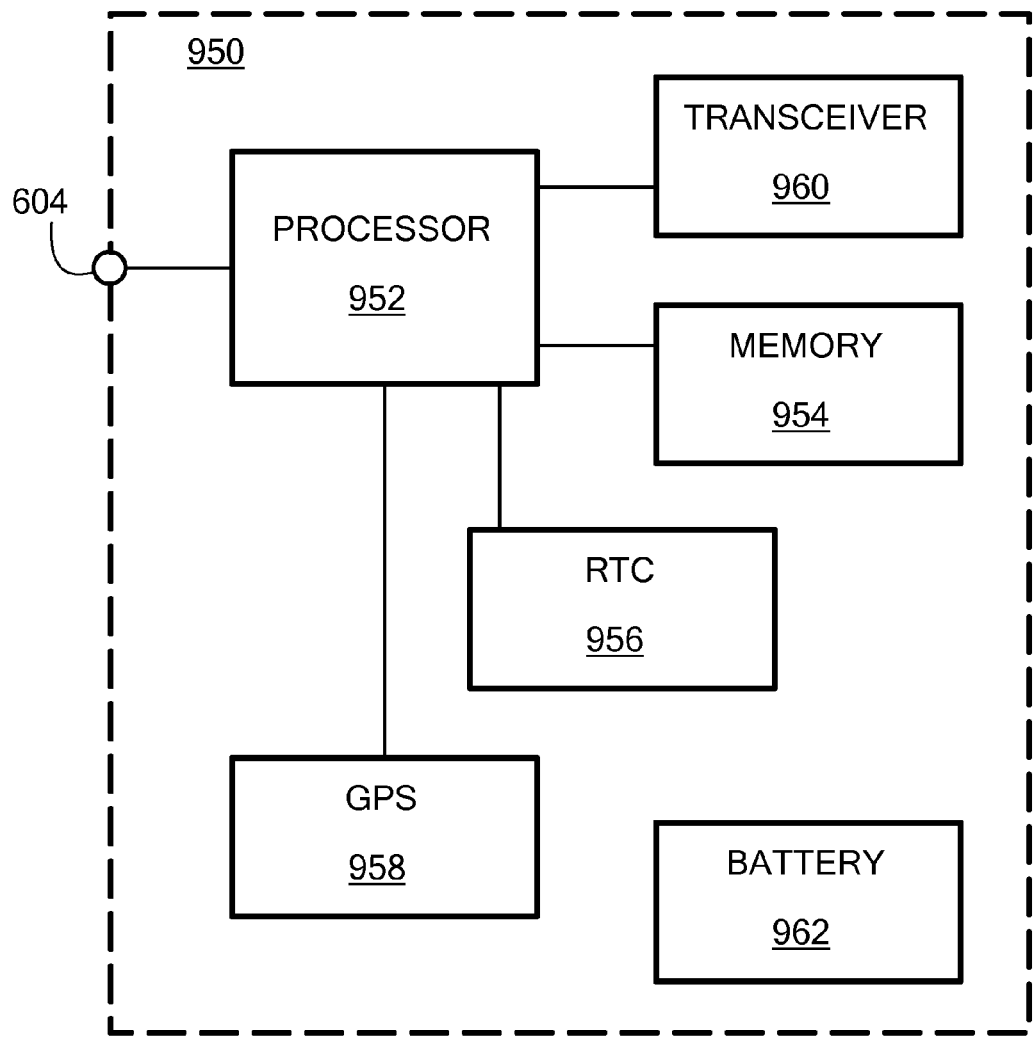
FIG. 10 is a block diagram of a system in accordance with an embodiment of the present invention.

As described above, each connector 112, 204 is provided to allow a signal to be passed along any length of pipeline desired by connecting the output electrical or optical signal from one end of a sensor tape 100, 200 corresponding to an individual pipe segment to the input connector of the next sensor tape 100, 200 corresponding to the next pipe segment. Alternately, each pipe segment comprising an individual unit within a pipeline system may have, in addition to connectors on both ends, a system 950, implemented as, for example, an integrated circuit device, which can have monitoring functions built into its microprocessor platform with associated software, as shown in FIG. 10. The system 950 may be integrated into a connector 112, 204.

The device 950 may include a processor 952 and a memory 954 that can hold data identifying a respective pipe segment in the pipeline system, such as a unique pipe segment address that allows for identification of the specific pipe segment location where a detected problem has occurred. The device 950 can have a real-time clock 956 for time and date information that facilitates identification of the detected event. In addition, a GPS device 958 may be included to provide specific location information. Of course, if the location is static, i.e., not moving, then a GPS device may not be needed and the static location information can be stored in the memory 954. Alternatively, the device 950 can act as a node to transmit status data through any modality such as, for example, satellite, wire, wireless, and/or internet, for example, with an appropriately configured transceiver 960. The system may be powered by a battery 962 that can be charged by solar power, for example. A device such as the Snapdragon™ processor available from Qualcomm Incorporated may be used.

Further, in the application to a pipeline, as each pipe segment is installed in the pipeline, a real time test of conductivity of the sensor tape 100, 200 can be instituted for each electrical wire or optical fiber embedded in the tape strip as it is wrapped around the pipe segment. The test signal detected in this initial wrapping insures that any problems in connectivity are immediately detected in real-time to optimize cost and performance functions.

Still further, embodiments of the present invention allow for testing the integrity of an entire system and for detecting the falsification of the signal indicating that no incursion or excursion has been detected because of the fail-safe nature of the system and its binary output (signal/no-signal). If, for example, a third party were interfering with the output signal and had over-ridden it to always indicate a safe condition, the operator could test for this by turning off power to the sensors and determining whether or not the output of the system changes state. Of course, either the entire system could be turned off or only one or more of the sensor segments. If the output signal does not change in response to all, or part, of the system being shut down, then there may be some interference with the system in progress, such as electronic cloaking.

Embodiments of the present invention may also be made of materials and components that are meant to reduce the cost or enhance performance in order to make the tape sensor either disposable or for single-use. Thus, for example, the tape may be thinner, such as for packing applications, where removal of the tape when opening the package permanently renders the tape inoperative. Alternatively, the adhesive on the tape could be made stronger to enhance structural and/or thermal stability of the fabric mesh openings. In addition, the components within the connector may have less functionality, in order to reduce cost, and, therefore, lend themselves to disposable applications.

Known installations of detector sheets include a process of applying a resin and then having to wait for the resin to reach a point of tackiness for subsequent attachment of the sensor sheet. Advantageously, embodiments of the present invention simplify the fabrication and installation of a sensor system. As described above, the sensor tape 100, 200 has silicone rubber laminated or applied on both sides and forms a multilayer tape. In one example, this might be provided as a roll of rubberized tape with the sensor sandwiched in the middle, for example, measuring 6 inches wide and 250 feet long to allow for use in a "spin wrap" process, well known to those in the pipeline insulation wrapping business, to rapidly encapsulate a pipe for a pipeline to be protected by the tamper proof tape to provide for detection of an intrusion/extrusion event.

Embodiments of the present invention produce a binary fail-safe, self-monitoring, reliable, durable, passive and robust tape/fabric sensor system able to withstand the rigors of harsh environmental conditions such as experienced by a pipeline or cargo container. Embodiments of the present invention can be utilized in both aboveground and underground pipeline systems and can be applied as new construction in a factory or as a field installed retrofit.

In an electrical wire version of the invention, the adjacent portions of the wire can be of suitable spacing to provide RFI/EMI shielding. The wrapped object can thereby be isolated from outside electromagnetic interference or RF or other electromagnetic emissions from the wrapped object can be blocked.

Figure 14:
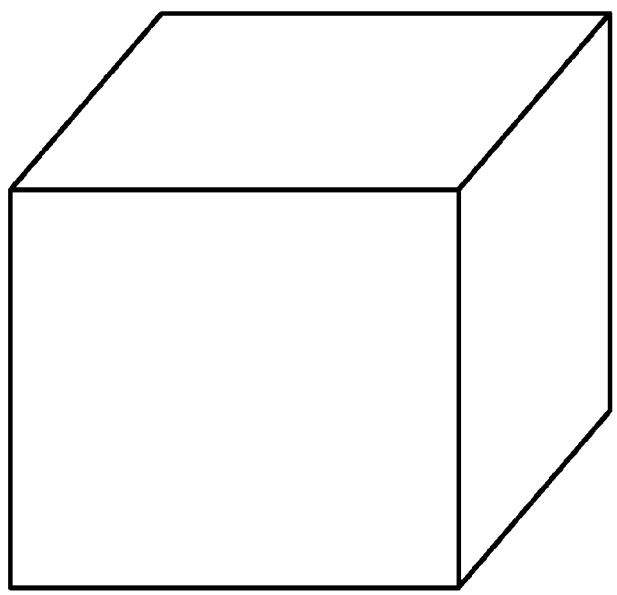
FIG. 14 is a diagrammatic view of a pallet cover embodying the invention.

In a further aspect, the invention can be embodied in a pallet cover, such as shown in FIG. 14, or other cover or enclosure. The pallet cover in one implementation is six sided to cover the top, bottom and four sides of a pallet and contents thereon. In another implementation, the pallet cover has five sides which include a top and four sides which fit over the object on the pallet. The pallet itself can be separately secured by a sensor sheet in the pallet floor in this latter version.

The pallet cover including the security sheet can be fabricated in two or more pieces or panels to form a four sided or other multi-sided cover to fit over an object placed on the pallet. The cover may be of cylindrical or other rounded shape or multi-sided depending upon the shape of the object on the pallet. In one embodiment, the cover is formed by panels or sheets which are stitched or otherwise seemed or bonded to form a substantially continuous flexible cover. The electrical wire or optical fiber filament which forms the signal path extends across substantially the entire area of each of the panels and the filament of each panel is connected together by suitable connectors to provide a single continuous signal path for the entire cover. Alternatively, a continuous signal path can be provided for each respective panel of the cover and coupled via an appropriate logic gate to detection circuitry such that a break in the wire or fiber of any one or more panels will signal an alarm condition.

Having thus described several features of at least one embodiment of the present invention, it is to be appreciated that various alterations, modifications, and improvements will readily occur to those skilled in the art. Such alterations, modifications, and improvements are intended to be part of this disclosure and are intended to be within the scope of the invention. Accordingly, the foregoing description and drawings are by way of example only, and the scope of the invention should be determined from proper construction of the appended claims, and their equivalents.

What is claimed is:

1. A security tape comprising:
   a flexible woven mesh sensor strip having a first side and an opposite side;
   a filament woven in the mesh sensor strip providing a single constant continuous signal path across substantially the entire area of the strip;
   the mesh strip having a woven structure;
   a first layer of flexible insulative material adhesively bonded to the first side of the mesh strip;
   a second layer of flexible insulative material adhesively bonded to the opposite side of the mesh strip;
   the adhesive of the first and second layers extending into the woven structure of the mesh strip to fix the filament in position in the mesh strip;
   the signal path having a first end connectable to a first connector unit for introducing a signal into the signal path, and having a second end connectable to a second connector unit for receiving the signal from the signal path.

2. The security tape of claim 1 wherein the filament providing the single continuous signal path is one of an electrical wire or an optical fiber.

3. The security tape of claim 1 wherein the first and second layers of flexible insulative material are wider than the width of the sensor strip and are bonded together along and outward of the side edges of the sensor strip.

4. The security tape of claim 3 wherein the bonded portions of the first and second layers are sealed against moisture infiltration.

5. The security tape of claim 3 wherein at least one of the first and second layers is resistant to mechanical, chemical, thermal or environmental damage.

6. The security tape of claim 3 including an outer layer on at least one of the first and second layers that is resistant to mechanical, chemical, thermal or environmental damage.

7. The security tape of claim 1 in which the filament is an electrical wire having an array of adjacent portions spaced to provide RFI/EMI shielding.

8. The security tape of claim 1 wherein the adhesive infiltrates the interstices of the woven mesh strip to produce a unitary bonded sandwich composed of the first and second layers and interposed mesh strip.

9. The security tape of claim 1 wherein the adhesive infiltrates the interstices of the woven mesh strip to mechanically retain the filament in a stable position in the mesh strip.

10. The security tape of claim 1 wherein the adhesive infiltrates the interstices of the woven mesh strip to thermally stabilize the filament within the mesh strip.

11. The security tape of claim 1 in which the tape is incorporated in each panel of a pallet cover.

12. A security tape comprising:
   a flexible woven mesh strip having a predetermined width and a predetermined length, first and second sides and first and second ends;
   a plurality of separate and parallel signal paths woven in the mesh strip and arranged along the predetermined length of the material strip, each signal path having a first end at one end of the predetermined length of the material strip and a second end at the other end of the predetermined length of the material strip and operative in a non-alarm condition to carry a signal;
   a first layer of flexible insulative material having an adhesive on a side bonded to the first side of the mesh strip;
   a second layer of flexible insulative material having an adhesive on a side bonded to the second side of the mesh strip;
   the adhesive of the first and second layers extending into the woven structure of the mesh strip to fix the signal paths in position;
   the plurality of first ends being connectable to a first connector for connecting adjacent pairs of the first ends of the plurality of signal paths to one another;
   the plurality of second ends being connectable to a second connector for connecting adjacent pairs of the second ends of the plurality of signal paths to one another;
   wherein the connected pairs of first ends and second ends by the first and second connectors, respectively, establish a single continuous signal path;
   the first connector operative to couple a signal from a signal source for transmission over the single continuous signal path;
   the second connector operative to couple the signal transmitted over the single continuous signal path to a signal detector; and wherein a break in any of the signal paths causes a loss of the signal transmitted over the single continuous signal path and indicative of an alarm condition.

13. The security tape of claim 1 wherein the side edges of the at least one of the first and second layers are raised.

14. The security tape of claim 12 wherein each of the signal paths is an electrical wire and the first and second connectors couple the first and second ends of the signal paths to carry an electrical signal.

15. The security tape of claim 12 including:
a second security tape overlaid on the first security tape in an offset manner to effectively create a solid wall of detection.

16. The security tape of claim 12 wherein each of the signal paths is an optical fiber and the first and second connectors couple the first and second ends of the signal paths to carry an optical signal.

17. The security tape of claim 12 in which the tape is incorporated in each panel of a pallet cover.

* * * * *